US008598326B2

(12) United States Patent
Nueesch et al.

(10) Patent No.: US 8,598,326 B2
(45) Date of Patent: Dec. 3, 2013

(54) POLYNUCLEOTIDE ENCODING A FUSION POLYPEPTIDE SUITABLE AS CYTOTOXIN

(75) Inventors: Jurg Nueesch, Heidelberg (DE); Jean Rommelaere, Heidelberg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 352 days.

(21) Appl. No.: 12/496,179

(22) Filed: Jul. 1, 2009

(65) Prior Publication Data

US 2010/0144847 A1 Jun. 10, 2010

Related U.S. Application Data

(63) Continuation of application No. 11/262,356, filed on Oct. 28, 2005, now abandoned, which is a continuation-in-part of application No. PCT/EP2004/004477, filed on Apr. 28, 2004.

(30) Foreign Application Priority Data

Apr. 30, 2003 (EP) .................................... 03009952

(51) Int. Cl.
*C07H 21/02* (2006.01)
*C12P 21/04* (2006.01)

(52) U.S. Cl.
USPC ........................................ 536/23.1; 435/69.7

(58) Field of Classification Search
None
See application file for complete search history.

(56) References Cited

U.S. PATENT DOCUMENTS

2006/0078970 A1 4/2006 Nuesch et al.

FOREIGN PATENT DOCUMENTS

EP 01077260 A 2/2001
EP 01275658 A 1/2003

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Astell, C., "The complete DNA sequence of minute virus of mice, an autonomous parvovirus", "Nucleic Acids Research", 1983, pp. 999-1018, vol. 11, No. 4.
Op De Beeck, A. et al., "NS1-and minute virus of mice-induced cell cycle arrest: Involvement of p53 and p21cip1", "Journal of Virology", Nov. 2001, pp. 11071-11078, vol. 75, No. 22.
Corbau, R. et al., "Phosphorylation of the Viral Nonstructural Protein NS1 during MVMp Infection of A9 Cells", "Virology", 1999, pp. 402-415, vol. 259, No. 2.
Corbau, R. et al., "Regulation of MVM NS1 by Protein Kinase C: Impact of Mutagenesis at Consensus Phosphorylation Sites on Replicative . . . ", "Virology", 2000, pp. 151-167, vol. 278, No. 1.
Gayle, Richard B., III, et al., "Identification of regions in interleukin-1 alpha important for activity", "The Journal of Biological Chemistry", Oct. 15, 1993, pp. 22105-22111, vol. 268, No. 29.

Kohl, A. et al., "The Rift Valley Fever Virus Nonstructural Protein NSs Is Phosphorylated at Serine Residues Located in Casein Kinase II.", "Virology", 1999, pp. 517-525, vol. 263, No. 2.

Lickert, Heicko, et al., "Casein kinase II phosphorylation of E-cadherin increases E-cadherin/beta-Catenin internation and strengthens cell . . . ", "The Journal of Biological Chemistry", Feb. 18, 2000, pp. 5090-5095, vol. 275, No. 7.

Litchfield, D., "Protein Kinase CK2; structure, regulation, and role in cellular decisions of life and death", "Biochem. J. ", 2003, pp. 1-15, vol. 369.

Nieset, Jill E., et al., "Characterization of the interactions of alpha-catenin with alpha-actinin and beta-catenin/plakoglobin", "Journal of Cell Science", 1997, pp. 1013-1022, vol. 110.

Nollet, Friedel, et al., "The role of the E-Cadherin/Catenin adhesion complex in the development and progression of cancer", "Molecular Cell Biology Research Communications", 1999 pp. 77-85, vol. 2.

Okamura, Heidi, et al., "p80/85 cortactin associates with the Src SH2 domain and colocalizes with v-Src in transformed cells", "The Journal of Biological Chemistry", Nov. 3, 1995, pp. 26613-26618, vol. 270, No. 44.

Pinna, L., "Protein kinase CK2: A challenge to canons", "Journal of Cell Science", 20002, pp. 3873-3878, vol. 115, No. 20.

Whisstock, James C., et al., "Prediction of protein function from protein sequence and structure", "Quarterly Reviews of Biophysics", 2003, pp. 307-340, vol. 36, No. 3.

* cited by examiner

*Primary Examiner* — Sheridan Swope
(74) *Attorney, Agent, or Firm* — Hultquist, PLLC; Steven J. Hultquist

(57) ABSTRACT

The present invention relates to fusion polypeptides including (a) a binding site for a cytoskeleton component and ($b_1$) an effector protein or the catalytic domain thereof or ($b_2$) a binding site for the effector protein, and nucleic acid sequences encoding the fusion polypeptides. Moreover, various therapeutic uses of the fusion polypeptides are described, e.g., the treatment of diseases associated with the presence of an aberrant cell population, preferably cancer or AIDS.

9 Claims, 6 Drawing Sheets

POLYNUCLEOTIDE ENCODING A FUSION POLYPEPTIDE SUITABLE AS CYTOTOXIN

CROSS-REFERENCE TO RELATED APPLICATIONS

This application is continuation of U.S. patent application Ser. No. 11/262,356, filed on Oct. 28, 2005, and published on Apr. 13, 2006 as U.S. Patent Application Publication No. 2006/0078970A1, now abandoned, which is a Continuation-in-Part application of and claims priority to PCT International Application No. PCT/EP2004/004477 filed on Apr. 28, 2004 and published on Nov. 11, 2004 as WO 2004/096858, which in turn claims priority to European Patent Application No. 03009952.7 filed on Apr. 30, 2003, the contents of which are incorporated herein by reference for all purposes.

BACKGROUND OF THE INVENTION

1. Field of Technology

The present invention relates to fusion polypeptides comprising (a) a binding site for a cytoskeleton component and ($b_1$) an effector protein or the catalytic domain thereof or ($b_2$) a binding site for said effector protein, and nucleic acid sequences encoding said fusion polypeptides. Furthermore, the present invention relates to various therapeutic uses of said fusion polypeptides, e.g., the treatment of diseases associated with the presence of an aberrant cell population, preferably cancer or AIDS.

2. Discussion of Related Art

For many reasons it is desirable to generate and use toxins that preferentially kill neoplastically transformed cells. In the past, this has been achieved with chemical compounds (cytotoxins, cytostatica), which with more or less specificity enabled a successful cancer treatment after surgery. Besides selectivity, a main problem of such compounds consists in the side effects but also in the lack of proficient targeting of the substance, which leads to the requirement for relatively high doses. One way to circumvent this problem is thought to be brought about by the use of targeted genetics using recombinant viruses to bring genetic elements into the tumors leading to an onsite expression of the toxin. Autonomous parvoviruses such as KRV, MVM or H-1 have been shown to preferentially propagate in and to kill neoplastically transformed cells. In addition, they consist of a class of viruses that, despite causing viremia in their infected host, mostly produce an apathogenic infection. For these reasons, autonomous parvoviruses are thought to be excellent tools for cancer gene therapy. Particular interests are focused on recombinant vectors maintaining their natural oncotropism, as well as their oncolytic and oncosuppressive potential. However, so far, little is known about the nature of the oncosuppressive potential of parvoviruses (which is independent of the parvoviral replicon) and, accordingly, the therapeutic use of said viruses, e.g., incorporated in heterologous systems such as recombinant adenoviruses or Measles viruses, for targeted gene therapy, e.g. cancer therapy is still in its infancy.

SUMMARY OF THE INVENTION

Thus, the technical problem underlying the present invention is to provide parvovirus based means for gene therapy, in particular for targeted cancer therapy, which overcome the disadvantages of the prior art therapeutic methods, e.g., as regards side effects and lack of specificity.

The solution to said technical problem is achieved by providing the embodiments characterized in the claims. The experiments resulting in the present invention were based on the observations that the main component involved in cell killing and hence, oncolytic activity of autonomous parvoviruses consists of NS1, the major nonstructural protein, which plays a key role during replication of progeny virus particles. The characterization of NS1 revealed a multifunctional protein endowed with a variety of enzymatic and regulatory functions, which have to act in a coordinated manner during a productive infection. Particularly, it was shown that the cytotoxic functions of NS1 were dependent upon the integrity of (PKC) phosphorylation sites, which led to the dissection (at least in part) of NS1 replicative functions from its cytotoxic activities by site-directed mutagenesis. In order to design new eventually more efficient and specific toxins it is important to understand the mechanisms for the NS1 induced selective killing and in consequence to eliminate undesired eventually even contraproductive functions of the polypeptide.

With these perspectives, new (desirably small) polypeptides/compounds with distinct features were designed on the basis of NS1 induced cell killing, independent on the replicative functions of the polypeptide. By analyzing the cytotoxic functions of NS1, it was shown that rather distinct regions of the polypeptide are important for cell killing than its enzymatic activities. These findings led to the conclusion that distinct regions of NS1 might specifically interact with cellular partner proteins and that the cytotoxic activity(ies) consist of a multiprotein complex assembled through NS1 rather than a catalytic activity of the viral protein alone. In addition, mutagenesis at conserved consensus PKC phosphorylation sites led to obliteration of the toxic activities of NS1, suggesting a strong regulation of this NS1 property. Initial studies leading to the present invention implied that such regulation of NS1 toxicity not only occurs in a timely coordinated manner by phosphorylation through distinct kinases, but also by the compartimentalization of the cell, leading to the conclusion that NS1 targeting to the site of action is an additional feature of regulation.

Two partner proteins could be identified which bind with high affinity to wild type NS1, however, lack affinity to site-directed NS1 mutants deficient for cytotoxicity. Thus, casein kinase II α binding to the region around S473 and tropomyosine binding to the region around T363 of NS1 could be identified. Analyses of NS1 impact to the host cell have presented multiple effects, which could lead to cytostasis and/or induction of cytolysis. Some of them might only be side effects of NS1 replicative functions, whereas others are induced specifically to release progeny virus particles from infected cells. The latter NS1 activities are of particular interest to design new drugs. Besides cell cycle arrest in S-phase of infected cells, expression of NS1 protein alone leads to dramatic morphological changes (cell shrinking), manifested by a disorganization of the cytoskeleton in susceptible cells. More detailed analyses have shown that after MVM infection of A9 cells predominantly tropomyosin and vimentin filaments are affected, while microtubles remain unaffected, indicating a selective impact of the NS1 protein to the host cell. In part, the dynamics of these cytoskeleton filaments seem to be under regulation of PKC, which in turn are dis-regulated upon MVM infection. More importantly, however, tropomyosin filaments are affected directly by complex formation of NS1 with CKIIα. These investigations led to the assumption that tropomyosin, a cytoskeleton component that is subject to alterations upon transformation, is targeted by NS1/CKIIα leading to cell death and eventually cytolysis. In particular, while tropomyosin 2 (TM2) is genuine target of CKIIαβ (the holoenzyme existing in eukaryotic cells), the high affinity interaction with NS1 forming the NS1/CKIIα complex does NS1/CKIIα complex does not recognize TM2 as a substrate anymore but is able to phosphorylate TM5 an alternative tropomyosin isoform. In consequence the tropomyosin filament structure becomes altered in the presence of the viral protein.

As previously mentioned, instead of its own enzymatic functions, NS1 induced cytolysis is rather dependent on the formation of a (multi)protein complex assembled by the viral protein through protein/protein interactions with (pre-existing) cellular polypeptides. Such protein complexes could have entirely different catalytic activities from the purified NS1 protein as characterized in extensive investigations. Particularly the NS1 interaction with the catalytic subunit of casein kinase II proposes a variety of new options. In fact, it could be shown that casein kinase II alters the substrate specificity in the presence of an NS1-oligomer, using for instance empty MVM capsids as substrate, which remain unaffected by recombinant highly active CKIIα/β complex. This observation leads to the conclusion that novel cellular targets can be phosphorylated and regulated through this NS1/CKIIα complex leading to cell death and cytolysis of MVM infected susceptible cells.

In addition to the interaction with a kinase, MVM NS1 has been shown to bind to tropomyosin as well. In fibroblasts Tropomyosin filaments are associated with filamentous actin. These filaments can be composed of different isoforms (Tropomyosin 1 to 5), which share large homologies in the primary structure. As part of the cytoskeleton, tropomyosin is also responsible for the intracellular organization and despite there is little known so far about the impact of tropomyosin for the organization of signaling pathways, in analogy to microtubules they could serve as scaffold proteins anchoring larger regulatory complexes at distinct locations within the cytoplasm. With this background, the NS1 interaction with this cytoskeleton component might on the one hand be important to target the (cytotoxic) NS1/CKIIα complex to a distinct location within an infected cell, on the other hand tropomyosin itself might be a target for regulation by this "novel kinase". Interestingly, recently evidence was obtained that tropomyosin is differentially phosphorylated by CKIIα/β compared to NS1/CKIIα in vitro and using cell lines overexpressing mutant CKIIα a different phosphorylation pattern of tropomyosin in infected cells was observed. Moreover, these cell lines showed a certain resistance towards MVM induced alterations of the cytoskeleton and in consequence cell killing compared to the parental A9 fibroblasts.

In regard to these results, it was proposed that NS1 mediated targeting of CKIIα to tropomyosin leads to dramatic morphological alterations of the host cell and eventually cell death, which could be a prerequisite for MVM induced cell lysis. To proof this hypothesis, constructs were generated which are able to target wild type of endogenous CKIIα to tropomyosin. These constructs were tested for their impact on cell survival and it was found that specific cytotoxicity could be induced by NS1 targeting of CKIIα to tropomyosin, i.e. that these constructs are suitable for targeted gene therapy, preferably targeted cancer therapy. The findings of these experiments also suggest that NS1 (or parts of it) mediates CKII kinase activity within the cell by either one, (i) targeting the catalytic enzyme within the cell to appropriate subcellular compartments and (ii) mediating the substrate specificity of this enzyme.

DETAILED DESCRIPTION OF THE INVENTION

The peptide of the invention is a fusion polypeptide combining a binding site for a cytoskeleton component (e.g. tropomyosin) (i.e. a targeting site), an effector protein, e.g. a protein kinase, or a binding site for an effector protein, e.g., a protein kinase (e.g. casein kinase II; CKIIα). Since both elements can be very short (e.g., $CKII_\beta$ consists only of a dekapeptide), the two elements can be spaced by a "stufferpeptide" (e.g., enhanced green fluorescent protein; EGFP to enhance accessibility of both sites and stability of the toxin. The peptide can be applied as a genetic element or a compound and could/should harbor desired regulatory elements such as signals for post-translational modifications (e.g. phosphorylation sites) altering the specificity, additional signaling peptides (e.g. for secretion), and/or degradation signals controlling the stability. In order to increase specificity, the nucleic acid sequence encoding the fusion polypeptide of the invention can be placed under control of constitutive or inducible (including tissue specific) promoters and packaged into recombinant particles harboring targeting signals for appropriate cell/tissue specificity.

Thus, in a first embodiment, the present invention relates to a fusion polypeptide comprising (a) a binding site for a cytoskeleton component and ($b_1$) an effector protein or the catalytic domain thereof or ($b_2$) a binding site for said effector protein.

Parts (a) and (b) may comprise wild type sequences as well as sequences differing from the wild type sequences, e.g. by deletion(s), substitution(s) and/or addition(s) of amino acids. Such differences may result in peptides exhibiting improved or new biological activities, e.g., an improved binding of a cytoskeleton component.

Both parts (a) and (b) are preferably linked by covalent bond. Alternatively, other non-covalent interactions between the two elements (a) and (b) are possible. The orientation between the two elements (a) and (b) is interchangeable. Preferably, part (a) forms the N-terminal part of the fusion polypeptide.

In a preferred embodiment, both parts (a) and (b) of said fusion protein are linked by a suitable (poly)peptide linker, e.g., ensuring (i) that parts (a) and (b) can interact with their partners and/or (ii) that the fusion polypeptide has sufficient stability. Suitable (poly)peptide linkers are known to the person skilled in the art and, can very in length considerable. Examples of suitable (poly)peptide linkers are EGFP, or other inert soluble proteins such as croE, which are generally used to stabilize peptides for immunization purposes. Alternatively, short random polypeptide stretches can be sufficient to separate the two elements (a) and (b).

Figure 5:
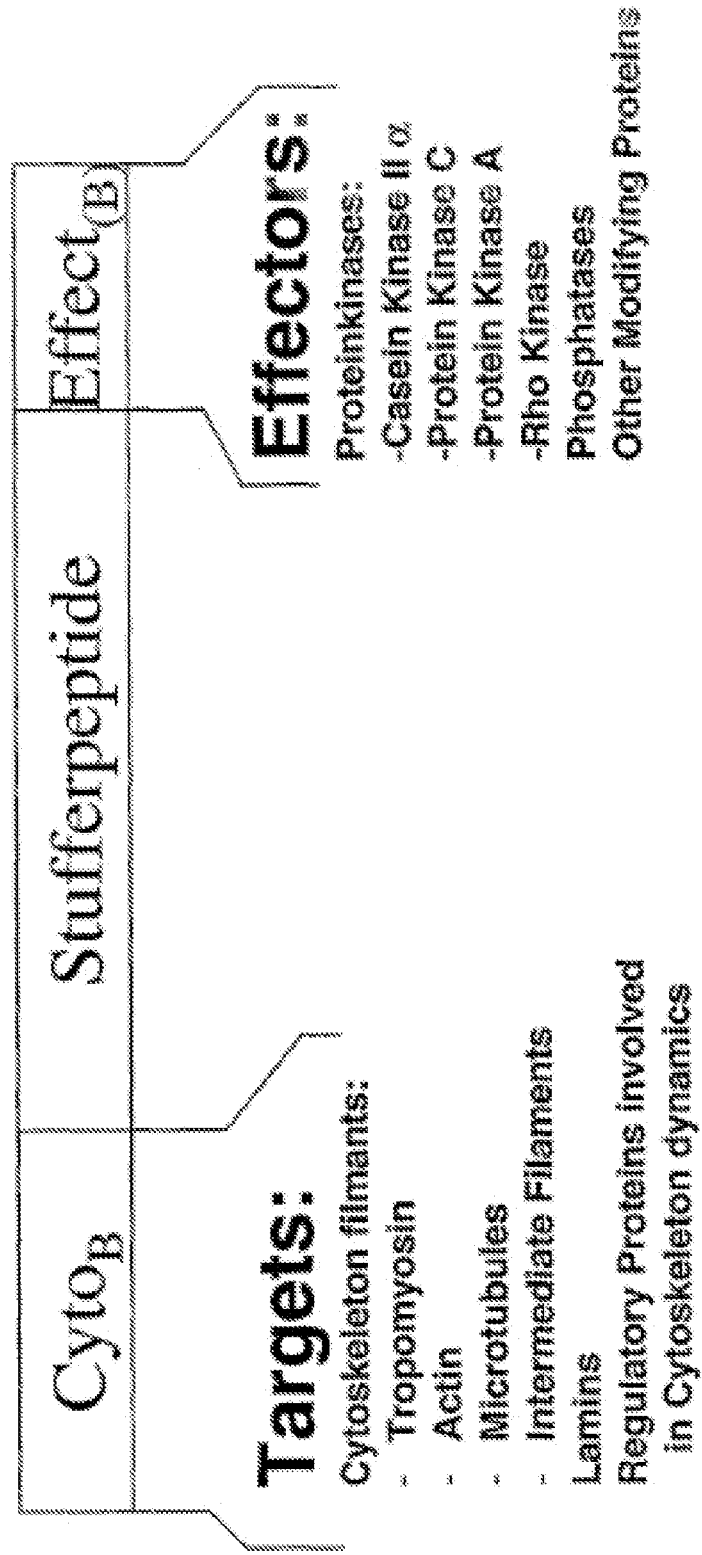
FIG. 5 illustrates targets and effectors combined by fusion polypeptides according to the invention.

Dramatic effects of targeting the catalytic subunit of casein kinase II, CKIIα to tropomyosin could be shown; see Example 2. Similarly, since other cytoskeleton and/or nuclear filaments are subject for regulation of their polymerization and depolymerization properties, it is possible to design other fusion polypeptides (toxins) analogous to the fusion polypeptide of Example 1 containing alternative effector proteins or binding sites thereof (e.g. other protein kinases, phosphatases, enzymes exerting other post-translational modifications), which are able to destabilize or stabilize the cytoskeleton or nuclear lamina according to the desired effects. This effectors could either be targeted to tropomyosin or alternatively to other cytoskeleton filaments, lamins and/or regulatory components involved in polymerization/depolymerization of the filaments, such as cofilin or profilin. The latter seems to be involved in the polymerization activity of tropomyosin and is subject to regulation through PKCλ, which is subject to regulation by MVM NS1 protein. Both effects, the targeting of CKIIα to tropomyosin leading to restructuring of tropomyosin and the reduction of polymerization activity through PKCλ/profilin through NS1 are able to damage the host cell and in consequence inducing cell death. Therefore, it can be expected that the principle of the present invention is useful for inducing destruction (or reorganization) of the cytoskeleton by targeting alternative components (cf. FIG. 5).

Thus, cytoskeleton components useful for binding by the fusion polypeptide of the invention comprise cytoskeleton filaments like tropomyosin, actin, microtubules, intermediate filaments etc., lamins or regulatory proteins involved in cytoskeleton dynamics (e.g., polymerization/depolymerization), e.g., cofilin or profilin) with tropomyosin being preferred. Recent investigations have shown that tropomyosin is not the only (cellular) target of CKIIα that is subject to differential phosphorylation in the presence of NS1. Thus, particularly gelsolin was identified, an actin severing protein (modulator of actin filaments) whose phosphorylation pattern is altered by the complex formation of NS1 with CKIIα, and tubulin. Moreover, it was found that viral NS2 proteins might be further candidates for altered phosphorylation of CKα through interaction with NS1. Considering that MVM capsids become substrate for CKIIα in the presence of NS1 it can be expected that the interaction of NS1 is a key-element for MVM induced oncolytic activities. This conclusion is supported by the findings that cell lines expressing a dominant-negative mutant form of CKIIα become highly resistant for virus induced cytopathic effects.

Effector proteins useful for the fusion polypeptide of the invention comprise protein kinases, phosphatases, enzymes exerting other post-translational modifications etc. which are able to destabilize or stabilize the cytoskeleton or nuclear lamina according to the desired effects with casein kinase (CKIIα) being preferred.

In a more preferred embodiment of the fusion polypeptide of the invention, the binding site is derived from parvovirus NS1, e.g. the Tropomyosin binding region of TnT, or the Tropomyosin binding subunit of Troponin.

In an even more preferred embodiment of the fusion polypeptide of the invention, the binding site for the cytoskeleton component comprises the amino acid sequence from positions 235 to 379 of NS1 (included in SEQ ID NO: 11) (Astell et al., 1983, Nucl. Acids Res. 11, 999-1018).

Particularly preferred is a fusion polypeptide of the invention, wherein part (b) is a binding site for casein kinase II (CKIIα) comprising the amino acid sequence DLEPDEELED (SEQ ID NO: 1).

Figure 4:
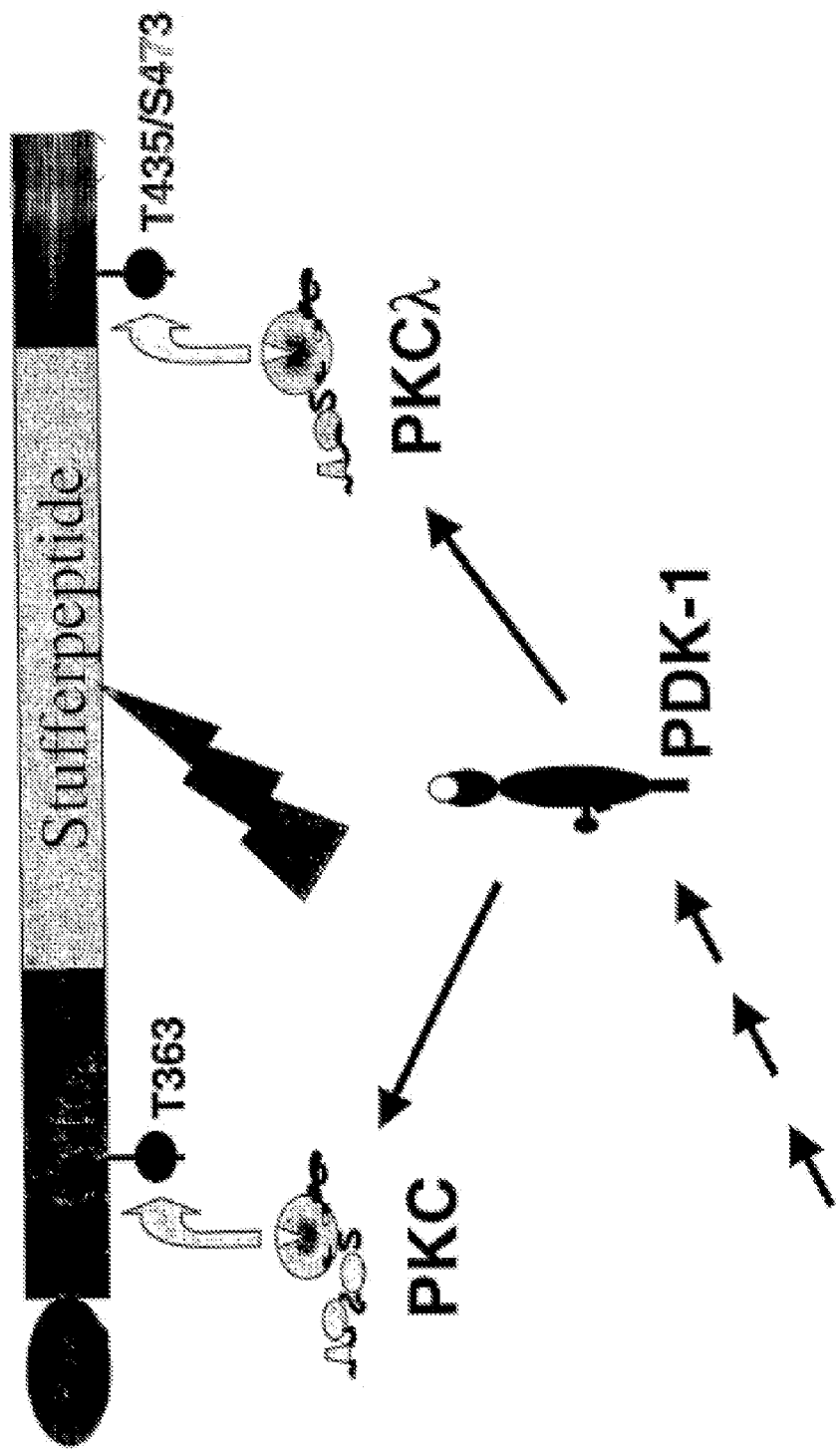
FIG. 4 illustrates NS1 phosphorylation through protein kinases.

To enhance the specificity of the fusion polypeptide of the invention as a toxin, e.g., for neoplastically transformed cells, it might be desirable to include regulatory features. In the experiments shown in Examples 1 and 2, the NS1 interaction domain with tropomyosin contains PKC phosphorylation sites, of which T363 upon mutagenesis to alanine obliterates binding to TM and in consequence reduces the toxic potential of NS1. Likewise, the other domain of NS1 interacting with CKIIα is phosphorylated by PKCλ at two amino acids T435 and S473, which seem to be crucial for NS1 to induce morphological alterations. NS1 mutants that abolish interaction with CKIIα are rather well tolerated by the host cell in comparison to the wild type polypeptide. Since members of the PKC family are often upregulated upon transformation, it seems possible that phosphorylation-dependent interaction with the appropriate cellular proteins is a feature for the oncolytic activity of autonomous parvoviruses. Thus, the fusion polypeptide of the invention could be attributed with this or similar features in order to render the interaction-site cell type specific, particularly for transformed cells. Such signals may consist of specific phosphorylation sites for target kinases, but also for acetylation-, methylation-, myristilation-, palmitylation- or other signals for post-translational modifications. In addition, the fusion polypeptide of the invention could contain signals, which induce conformational changes in order to expose the interaction sites upon a desired signal, analogous to the activation cascade of protein kinase C, or it could contain additional targeting and/or anchoring or secretion signal, such as NLS, NES, transmembrane domains, etc. (FIG. 4).

Thus, in a further preferred embodiment of the fusion polypeptide of the invention, modifications are present in parts (a) and/or (b) inducing or enhancing morphological changes of the host cell.

The fusion polypeptide of the invention may be used directly or it can be supplied to the cells by intracellular expression and subsequent secretion. Thus, the present invention also relates to a nucleic acid sequence encoding a fusion polypeptide of the invention as well as a recombinant vector containing said nucleic acid sequence. Preferably, the recombinant vectors are plasmids, cosmids, viruses, bacteriophages, cells, and other vectors usually used in the field of genetic engineering. Vectors suitable for use in the present invention include, but are not limited to the CMV-based expression vector for expression in mammalian cells and baculovirus-derived vectors for expression in insect cells. Preferably, the nucleic acid molecule of the invention is operatively linked to the regulatory elements in the recombinant vector of the invention that guarantee the transcription and synthesis of an mRNA in prokaryotic and/or eukaryotic cells that can be translated. The nucleotide sequence to be transcribed can be operably linked to a promoter like a T7, metallothionein I, polyhydrin, or CMV early promotor.

In a further embodiment, the present invention relates to recombinant host cells transiently or stably containing the nucleic acid sequences or vectors of the invention. A host cell is understood to be an organism that is capable to take up in vitro recombinant DNA and, if the case may be, to synthesize the fusion polypeptides encoded by the nucleic acid molecules of the invention. Preferably, these cells are prokaryotic or eukaryotic cells, for example mammalian cells, bacterial cells, insect cells or yeast cells.

The present invention also relates to an antibody that binds specifically to a fusion polypeptide of the invention. The term "antibody", preferably, relates to antibodies that consist essentially of pooled monoclonal antibodies with different epitopic specificities, as well as distinct monoclonal antibody preparations. Monoclonal antibodies are made from an antigen containing (fragments of) the polypeptides of the invention by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab') 2 fragments) which are capable of specifically binding to protein. Fab and f(ab')2 fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a FAB or other immunoglobulin expression library. Moreover, antibodies of the present invention include chimerical, single chain, and humanized antibodies.

For certain purposes, e.g. diagnostic methods or for assaying the half-life or clearance of the fusion polypeptide within an organism, the antibody of the present invention can be detectably labelled, for example, with a radioisotope, a bioluminescent compound, a chemiluminescent compound, a fluorescent compound, a metal chelate, or an enzyme.

The invention also relates to a transgenic non-human animal such as transgenic mouse, rats, hamsters, dogs, monkeys, rabbits, pigs, C. elegans and fish such as torpedo fish comprising a nucleic acid molecule or vector of the invention, preferably wherein said nucleic acid molecule or vector is stably integrated into the genome of said non-human animal, preferably such that the presence of said nucleic acid molecule or vector leads to the expression of a fusion polypeptide of the invention. Said animal may have one or several copies of the same or different nucleic acid molecules encoding one or several forms of said fusion polypeptide. This animal has numerous utilities, including as a research model for development/progression of carcinomas and therefore, presents a novel and valuable animal in the development of therapies, treatment, etc. for carcinomas. Accordingly, in this instance, the non-human mammal is preferably a laboratory animal such as a mouse or rat. It might be also desirable to inactivate expression or function of the fusion polypeptide at a certain stage of development and/or life of the transgenic animal. This can be achieved by using, for example, tissue specific, developmental and/or cell regulated and/or inducible promoters which drive the expression of, e.g., an antisense or ribozyme directed against the RNA transcript encoding the fusion polypeptide. A suitable inducible system is for example tetracycline-regulated gene expression as described, e.g., by Gossen and Bujard (Proc. Natl. Acad. Sci. 89 USA (1992), 5547-5551) and Gossen et al. (Trends Biotech. 12 (1994), 58-62).

Methods for the production of a transgenic non-human animal of the present invention, preferably transgenic mouse, are well known to the person skilled in the art. Such methods, e.g., comprise the introduction of a nucleic acid sequence or vector of the invention into a germ cell, an embryonic cell, stem cell or an egg or a cell derived therefrom. Production of transgenic embryos and screening of those can be performed, e.g., as described by A. L. Joyner Ed., Gene Targeting, A Practical Approach (1993), Oxford University Press. The DNA of the embryonal membranes of embryos can be analyzed using, e.g., Southern blots with an appropriate probe.

Due to the intrinsic cytotoxicity of the fusion polypeptide of the invention targeted at transformed cells, it can be used as an oncotoxin. The fusion polypeptide is able to target effector proteins (modifying cellular enzymes) to distinct targets within the cell in order to destroy or at least inhibit proliferation. Designed in the Examples to specifically kill cancer cells, however, the fusion polypeptide of the invention has a wider spectrum of action. Particularly, besides transformed cells, other aberrant cell populations (e.g. HIV infected cells) can be targeted and destroyed in a similar way, considering the specificity can be granted or at least enhanced compared to the healthy population. The fusion polypeptide of the invention has several advantages. As a genetic element, the specificity can be reached by targeted genetics and gene expression. Moreover, as exemplified with the parvovirus NS1 protein, binding sites and location within the cell can be further subject for regulation in order to achieve efficient cell killing in the desired environment. Last but not least, it is also possible to apply the fusion polypeptide of the invention directly as a compound attributed with the appropriate features. Treatment can be given to cell cultures or disease bearing organisms.

Thus, the present invention also relates to a pharmaceutical composition comprising a fusion polypeptide, nucleic acid sequence or recombinant vector of the invention and a pharmaceutically acceptable excipient, diluent or carrier. Examples of suitable pharmaceutical carriers etc. are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g. by intravenous, intraperetoneal, subcutaneous, intramuscular, topical or intradermal administration. The route of administration, of course, depends on the nature of the disease, its localisation and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of a disease, general health and other drugs being administered concurrently.

The delivery of the nucleic acid sequences of the invention can be achieved by direct application or, preferably, by using a recombinant expression vector such as a chimeric virus containing these compounds or a colloidal dispersion system. Direct application to the target site can be performed, e.g., by ballistic delivery, as a colloidal dispersion system or by catheter to a site in artery. The colloidal dispersion systems which can be used for delivery of the above nucleic acid sequences include macromolecule complexes, nanocapsules, microspheres, beads and lipid-based systems including oil-in-water emulsions (mixed), micelles, liposomes and lipoplexes. The preferred colloidal system is a liposome. The composition of the liposome is usually a combination of phospholipids and steroids, especially cholesterol. The skilled person is in a position to select such liposomes that are suitable for the delivery of the desired nucleic acid sequence. Organ-specific or cell-specific liposomes can be used in order to achieve delivery only to the desired tissue. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, e.g., an antibody, a receptor, sugar, glycolipid, protein etc., by well known methods). In the present invention monoclonal antibodies are preferably used to target liposomes to specific tissues, e.g., tumors, via specific cell-surface ligands.

Preferred recombinant vectors useful for gene therapy are viral vectors, e.g. adenovirus, herpes virus, vaccinia, Measles virus, Parvovirus, or an RNA virus such as a retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV)

and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957.

In order to achieve expression only in the target organ, e.g., a tumor to be treated, the nucleic acid sequences of the present invention can be linked to a tissue specific promoter and used for gene therapy. Such promoters are well known to those skilled in the art (see e.g. Zimmermann et al., (1994) Neuron 12, 11-24; Vidal et al.; (1990) EMBO J. 9, 833-840; Mayford et al., (1995), Cell 81, 891-904; Pinkert et al., (1987) Genes & Dev. 1, 268-76). For the treatment of a colon cancer, the use of a wnt-pathway specific promoter (Korinek et al., 1997, Science 275, 1784-1787) is preferred, for the HIV treatment use of a tat-responsive element. In addition, depending on the particular needs alternative available or newly designed promoter/enhancer elements can be used to drive expression of the nucleic acid sequence of the invention.

The present invention also relates to the use of the above compounds of the invention for the preparation of a pharmaceutical composition for the treatment of a disease associated with the presence of an aberrant cell population. Preferred diseases are cancer and AIDS. Other diseases could include the genetic diseases altering the cellular structure such as the Wiscott-Aldrich-Syndrome, Cystis Fibrosis, or chronic viral diseases such as Heptatitis B and Hepatitis C.

Finally, the present invention also relates to the targeting and mediating of an effector protein, e.g., CKIIα (activity) by a protein like the NS1 protein or submolecular parts thereof to candidate cellular proteins such as tropomyosin, tubulin and gelsolin.

The following Examples illustrate the invention.

EXAMPLE 1

Figure 1:
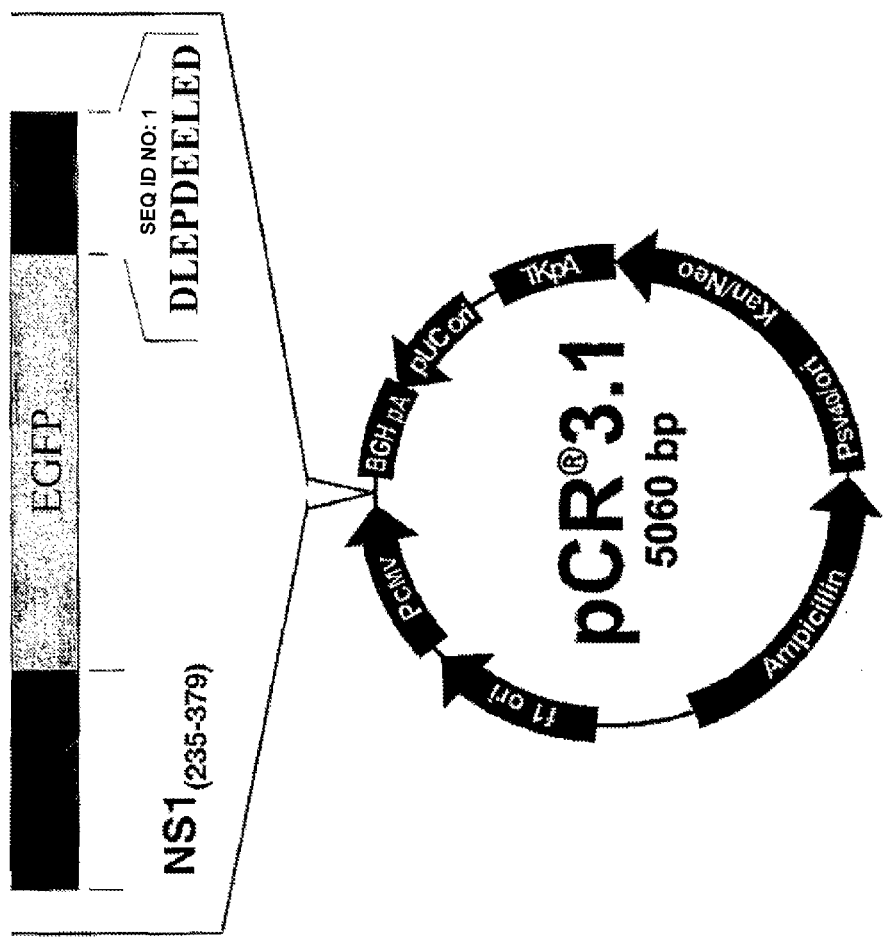
FIG. 1 shows constructs to test putative oncotoxins for their effects on host cells

Generation of Fusion Polypeptide Constructs for Testing Putative Oncotoxins for Their Effects on Mammalian Cells Given the supposition that NS1 works as a scaffold protein, connecting the catalytic subunit of casein kinase II (CKIIα) to tropomyosin, artificial peptides were designed harboring the tropomyosin binding region of MVM NS1 and connecting either CKIIα(or variants thereof) or just a known CKIIαbinding site (FIG. 1). PCR-derived fragments composed of a tropomyosin binding site ($TM_B$) derived from the parvovirus MVMp NS1 protein (amino acids 235 to 379 of SEQ ID NO: 11), the stabilizer polypeptide EGFP derived from pEGFP (Becton Dickinson, Heidelberg), and either a casein kinase IIαbinding site (derived from CKIIβ: DLEPDEELED; SEQ ID NO: 1) or the functional casein kinase II catalytic subunit CKIIα(NCBI L15618). ($CKII_B$) were cloned directly into pCR3.1 (Invitrogen, Karlsruhe), due to 3'adenosinetriphosphate overhangs generated by Taq-polymerase (see Annex 1). EGFP, an in eukaryotic cells tolerated protein, serves as a spacer and to stabilize the fusion polypeptide. The plasmid constructs were then transfected in eucaryotic cells A9, HEK 293 and the effector proteins were expressed under the control of the cytomegalo virus early promoter ($P_{cmv}$). In addition, the constructs contain a neomycin-resistance gene under the control of SV40 promoter/enhancer ($P_{SV40/ori}$), which allows for selection of transfected cells by their achieved resistance towards the drug G418. PCR fragments harboring the desired properties are directly ligated into the linearized pCR3.1 vectors, which contain 3' terminal T-overhangs according to the manufacturer's suggestions (Invitrogen, Karlsruhe). These expression plasmids are utilized to determine toxicity of an appropriate gene by colony formation inhibition assays by using G418 sensitive cell lines. Given the supposition that NS1 works as a scaffold protein, connecting the catalytic subunit of casein kinase II (CKIIα) to tropomyosin, artificial peptides were designed harboring the tropomyosin binding region of MVM NS1 and connecting either CKIIα(or variants thereof) or just a known CKIIαbinding site (FIG. 1). PCR-derived fragments composed of a tropomyosin binding site ($TM_B$) derived from the parvovirus MVMp NS1 protein (amino acids 235 to 379 of SEQ ID NO: 11), the stabilizer polypeptide EGFP derived from pEGFP (Becton Dickinson, Heidelberg), and either a casein kinase IIa binding site (derived from CKIIβ: DLEPDEELED; SEQ ID NO: 1) or the functional casein kinase II catalytic subunit CKIIα (NCBI L15618) isolated from the mouse fibroblast cell line A9. ($CKII_B$) were cloned directly into pCR3.1 (Invitrogen, Karlsruhe), due to 3' adenosinetriphosphate overhangs generated by Taq-polymerase (see Annex 1). EGFP, an in eukaryotic cells tolerated protein, serves as a spacer and to stabilize the fusion polypeptide. The plasmid constructs were then transfected in eucaryotic cells A9, HEK 293 and the effector proteins were expressed under the control of the cytomegalo virus early promoter ($P_{CMV}$). In addition, the constructs contain a neomycin-resistance gene under the control of SV40 promoter/enhancer ($P_{SV}$40/ori), which allows for selection of transfected cells by their achieved resistance towards the drug G418. PCR fragments harboring the desired properties are directly ligated into the linearized pCR3.1 vectors, which contain 3' terminal T-overhangs according to the manufacturer's suggestions (Invitrogen, Karlsruhe). These expression plasmids are utilized to determine toxicity of an appropriate gene by colony formation inhibition assays by using G418 sensitive cell lines.

The following effector constructs were generated and analyzed for their impact on colony formation inhibition: $TM_B$-CKIIα (the catalytic subunit of casein kinase II (CKIIα) linked to a tropomyosin binding site (derived from parvovirus MVM NS1 protein) spaced by GFP)) and $TM_B$-$CKII_B$ (an adaptor construct harboring the binding sites for tropomyosin as well as a casein kinase II (CKIIα) binding site). The two binding sites are fused to the enhanced green fluorescent protein (EGFP). As negative controls, the following pseudo-effector constructs were generated: GFP-CKIIα (casein kinase IIα linked to GFP without a tropomyosin binding site), $TM_B$-E81A (tropomyosin binding site linked through GFP to a catalytic inactive casein kinase IIα), $TM_B$-GFP (tropomyosin binding site of NS1 linked to GFP without CKIIα or $CKII_B$).

EXAMPLE 2

Toxicity Assays

Figure 2A:
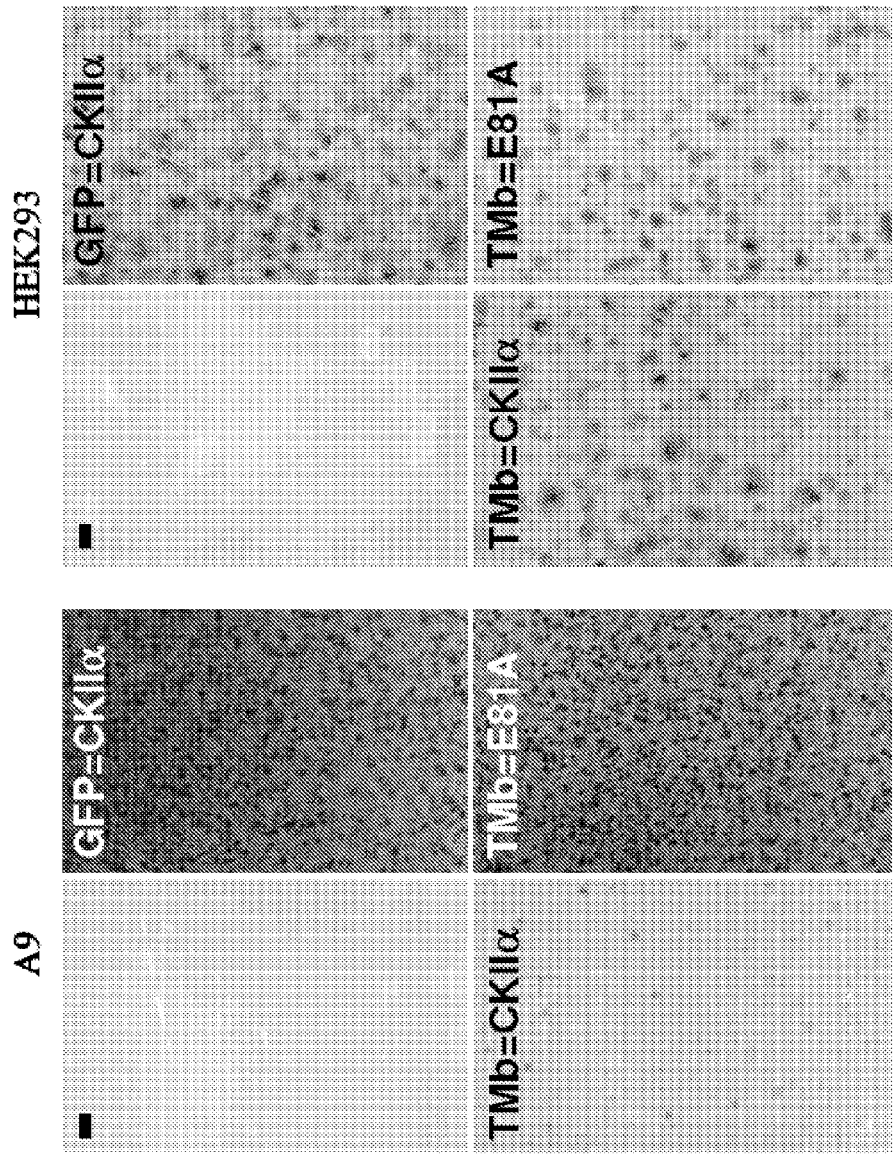
FIG. 2 shows results of toxicity assays and colony formation inhibition assays performed with the constructs described in Example 1.
Figure 2B:
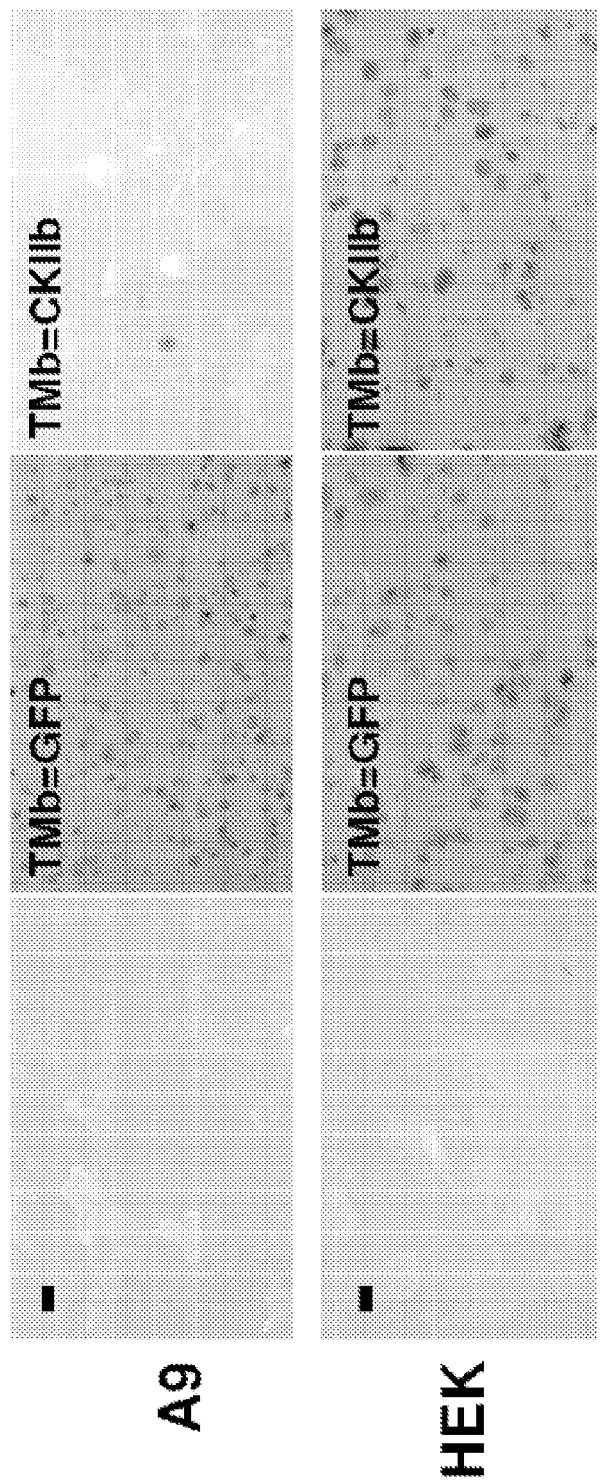
Figure 3:
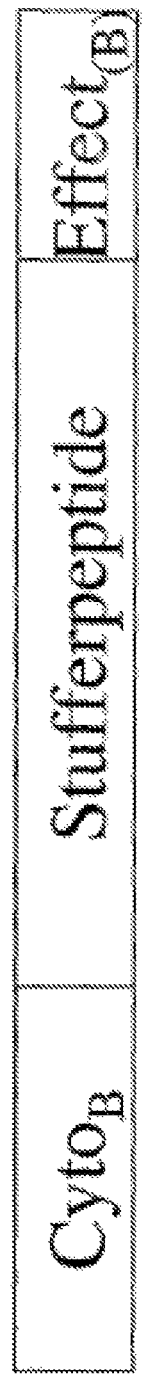
FIG. 3 illustrates a fusion polypeptide according to the invention.

Colony formation inhibition assays were performed with the constructs described in Example 1. A9 or HEK293 ($2 \times 10^5$ cells per 25 cm$^2$) were transfected with 10 µg plasmid DNA using 25 µl lipofectamin in DMEM without serum according to the manufacturer's conditions (Invitrogen). After 5 hr incubation transfection medium was replaced with DMEM containing 10% FBS and cells were grown for additional 48 h in absence of G418 before subdividing into 150 cm$^2$ plates where transfected cells were selected for by addition of 400 µg/ml G418 (SIGMA, Taufkirchen). Growing colonies were fixed and stained according to McCoy after two to three weeks growth under selective pressure. Two representative experiments are shown in FIG. 2a and FIG. 2b. While expression of the two effector proteins ($TM_B$=CKIIα (FIG. 2a) and $TM_B$=CKII$_B$ (FIG. 2b) allowed only few colonies to be generated in A9 cells in comparison to the control peptides, almost similar transfectants were generated in a low passage HEK293 cell lines, reflecting the selective toxicity of the fusion polypeptide of the invention.

Thus, in the presence of the designed toxin (e.g. $TM_B$-GFP-CKIIα or $TM_B$-GFP-CKII$_B$), hardly any colonies could be obtained after transfection of the MVM susceptible fibroblast cell line A9, while the transfections of the plasmids expressing the control peptides (peptides that do not connect CKIIα) generated >2000 colonies under G418 selection. It should be mentioned that all transfections delivered green fluorescent cells 2 days post transfection, suggesting that the proteins were indeed expressed during a certain period. Interestingly, with $TM_B$-GFP-CKII$_B$ significantly less colonies were obtained than with GFP-NS1$_{wt}$ (data not shown), suggesting that in absence of additional regulatory elements present within the NS1 coding sequence, the newly designed toxin is more effective than the original viral protein. In contrast to the susceptible A9 cells, transfection of the effector constructs $TM_B$-CKIIα or $TM_B$-GFP-CKII$_B$ produced almost the same amounts of colonies in HEK293 cells, demonstrating that the newly designed toxins exert cell type specificity.

EXAMPLE 3

Generation of Semi-Synthetic Toxins by Chimeric PCR

Fusion constructs are generated by consecutive PCR reactions using overlapping primer pairs. In a first reaction the individual PCR-elements generated: TM$_B$(GFP): Lefthand primer A 5'-GATATCCCATGGGGAAAACTAACTTTT-TAAAAGAAGGCGA-3' (SEQ ID NO: 2) with righthand primer B: 5'-TCCTCGCCCTTGCTCACCATATG-GCAACTTAACATAGGT-3' (SEQ ID NO: 3) using pdB-MVp (Kestler et al,1999) as a template. (TM$_B$)-GFP.CKII$_B$: C: 5'-ACTATGTTAAAGTTTGCCATATGGTGAG-CAAGGGCGAGGA-3' (SEQ ID NO: 4) with D: 5'-GCG-GCCGCTCTAGATTAATCTTCCAATTCTTCATC-GGGTTCCAAATCCCTCC GATGCTTGTA-CAGCTCGTCCATGCCGAG-3' (SEQ ID NO: 5) using pEGFP (Becton Dickinson) as a template. GFP-(CKIIα): E: 5'-CCCGGGATGGTGAGCAAGGGCGAG-GAGCTGTTCACCGGGG-3' (SEQ ID NO: 6) and F: 5'-TC-CTCGCCCTTGCTCACCATCTGCT-GAGCGCCAGCGGCAGG-3' (SEQ ID NO: 7) using pEGFP as a template. (TM$_B$)-GFP-(CKIIα): Primer A and F using pEGFP as a template (GFP)-CKIIα(wt or E81A): G: 5'-CTGCCGCTGGCGCTCAGCAGATGGTGAG-CAAGGGCGAGGA-3' (SEQ ID NO: 8) and H: 5'-GCGGC-CGCTTACTGCTGAGCGCCAGCGGCAGCTGGTACGG-3' (SEQ ID NO: 9) using pCR2.1:mCKIIα or pCR2.1:CKII-E81A, respectively (Nhesch unpublished) as templates. (TM$_B$)-GFP: primer C and I: 5'-ACGGTCTCGATGAGC-GACCGGCGCTCAGTTGG-3' (SEQ ID NO: 10) with pEGFP as a template.

In a second PCR two individual elements were combined to a fusion-protein and amplified with N- and C-terminal primers:

TM$_B$-GFP; TM$_B$-(GFP) with (TM$_B$)-GFP using primer A and I.

TM$_B$-CKII$_B$: TM$_B$-(GFP) with (TM$_B$)-GFP-CKII$_B$ using primers A and D.

GFP-CKIIα: GFP-(CKIIα) with (GFP)-CKIIα(wt) using primers E and H.

(TM$_B$)-GFP-(CKIIα): TM$_B$-(GFP) with GFP-(CKIIα) using primers A and F.

In a third PCR the remaining triple fusion constructs were generated:

TM$_B$-CKIIα(wt): TM$_B$-GFP-(CKIIα) with (GFP)-CKIIα (wt) using primers A and H.

TM$_B$-CKIIα(E81A): TM$_B$-GFP-(CKIIα) with (GFP)-CKIIα (E81A) using primers A and H.

The final PCT+R constructs [TM$_B$-GFP, TM$_B$-CKII$_B$, GFP-CKIIα, TM$_B$-CKIIα(wt), AND TM$_B$-CKIIα(E81A)] were directly ligated into linearized pCR3.1 according to the manufacture's conditions (Invitrogen) and tested for their properties by sequencing (Microsynth GmbH, Balgach Switzerland).

That which is claimed is:

1. A recombinant nucleic acid sequence encoding a cytotoxic fusion polypeptide comprising a binding site for tropomyosin and a binding site for the effector protein CKIIα, wherein
   (a) the binding site for tropomyosin is the binding site from parvovirus minute virus of mice (MVMp) non-structural protein (NS-1) comprising the region around Thr363 in SEQ ID NO: 11 and
   (b) the binding site for CKIIα is the amino acid sequence DLEPDEELED (SEQ ID NO: 1).

2. A recombinant vector containing the nucleic acid sequence of claim 1, wherein the nucleic acid sequence is operatively linked to regulatory elements allowing transcription and synthesis of a translatable RNA in prokaryotic and/or eukaryotic host cells.

3. A recombinant host cell which contains the recombinant vector of claim 2.

4. The recombinant host cell of claim 3, which is a mammalian cell, a bacterial cell, an insect cell or a yeast cell.

5. The recombinant nucleic acid sequence of claim 1, wherein the binding site for tropomyosin consists essentially of the amino acid sequence from positions 235 to 379 in SEQ ID NO: 11.

6. The recombinant nucleic acid sequence of claim 5, wherein parts (a) and (b) of the fusion polypeptide are linked by a peptide linker.

7. The recombinant nucleic acid sequence of claim 6, wherein said peptide linker is enhanced green fluorescent protein (EGFP).

8. A recombinant vector containing the nucleic acid sequence of claim 5, wherein the nucleic acid sequence is operatively linked to regulatory elements allowing transcription and synthesis of a translatable RNA in prokaryotic and/or eukaryotic host cells.

9. A recombinant host cell which contains the recombinant vector of claim 8.

* * * * *

UNITED STATES PATENT AND TRADEMARK OFFICE
CERTIFICATE OF CORRECTION

| | | |
|---|---|---|
| PATENT NO. | : 8,598,326 B2 | Page 1 of 1 |
| APPLICATION NO. | : 12/496179 | |
| DATED | : December 3, 2013 | |
| INVENTOR(S) | : Juerg Nueesch | |

It is certified that error appears in the above-identified patent and that said Letters Patent is hereby corrected as shown below:

On the title page, item 75, the name of inventor "Jurg" should be --Juerg--

Signed and Sealed this
First Day of April, 2014

Michelle K. Lee
*Deputy Director of the United States Patent and Trademark Office*

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Asp Leu Glu Pro Asp Glu Glu Leu Glu Asp
1               5                   10
```

<210> SEQ ID NO 2
<211> LENGTH: 40
<212> TYPE: DNA
<213> ORGANISM: Artificial Sequence
<220> FEATURE:
<223> OTHER INFORMATION: Synthetic Construct

<400> SEQUENCE: 2
gatatcccat ggggaaaact aactttttaa aagaaggcga                    40

<210> SEQ ID NO 3
<211> LENGTH: 39
<212> TYPE: DNA
<213> ORGANISM: Artificial Sequence
<220> FEATURE:
<223> OTHER INFORMATION: Synthetic Construct

<400> SEQUENCE: 3
tcctcgccct tgctcaccat atggcaactt aacataggt                     39

<210> SEQ ID NO 4
<211> LENGTH: 40
<212> TYPE: DNA
<213> ORGANISM: Artificial Sequence
<220> FEATURE:
<223> OTHER INFORMATION: Synthetic Construct

<400> SEQUENCE: 4
actatgttaa agtttgccat atggtgagca agggcgagga                    40

<210> SEQ ID NO 5
<211> LENGTH: 78
<212> TYPE: DNA
<213> ORGANISM: Artificial Sequence
<220> FEATURE:
<223> OTHER INFORMATION: Synthetic Construct

<400> SEQUENCE: 5
gcggccgctc tagattaatc ttccaattct tcatcgggtt ccaaatccct ccgatgcttg    60
tacagctcgt ccatgccg                                            78

<210> SEQ ID NO 6
<211> LENGTH: 40
<212> TYPE: DNA
<213> ORGANISM: Artificial Sequence
<220> FEATURE:
<223> OTHER INFORMATION: Synthetic Construct

<400> SEQUENCE: 6
cccgggatgg tgagcaaggg cgaggagctg ttcaccgggg                    40

<210> SEQ ID NO 7
<211> LENGTH: 41
<212> TYPE: DNA
<213> ORGANISM: Artificial Sequence
<220> FEATURE:
<223> OTHER INFORMATION: Synthetic Construct

<400> SEQUENCE: 7
tcctcgccct tgctcaccat ctgctgagcg ccagcggcag g                  41

<210> SEQ ID NO 8
<211> LENGTH: 40
<212> TYPE: DNA
<213> ORGANISM: Artificial Sequence
<220> FEATURE:
<223> OTHER INFORMATION: Synthetic Construct -continued

<400> SEQUENCE: 8
ctgccgctgg cgctcagcag atggtgagca agggcgagga                              40

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
gcggccgctt actgctgagc gccagcggca gctggtacgg                              40

<210> SEQ ID NO 10
<211> LENGTH: 32
<212> TYPE: DNA
<213> ORGANISM: Artificial Sequence
<220> FEATURE:
<223> OTHER INFORMATION: Synthetic construct

<400> SEQUENCE: 10
acggtctcga tgagcgaccg gcgctcagtt gg                                      32

<210> SEQ ID NO 11
<211> LENGTH: 672
<212> TYPE: PRT
<213> ORGANISM: Minute Virus of Mice (MVM)

<400> SEQUENCE: 11

Met Ala Gly Asn Ala Tyr Ser Asp Glu Val Leu Gly Ala Thr Asn Trp
1               5                   10                  15

Leu Lys Glu Lys Ser Asn Gln Glu Val Phe Ser Phe Val Phe Lys Asn
            20                  25                  30

Glu Asn Val Gln Leu Asn Gly Lys Asp Ile Gly Trp Asn Ser Tyr Lys
        35                  40                  45

Lys Glu Leu Gln Glu Asp Glu Leu Lys Ser Leu Gln Arg Gly Ala Glu
    50                  55                  60

Thr Thr Trp Asp Gln Ser Glu Asp Met Glu Trp Glu Thr Thr Val Asp
65                  70                  75                  80

Glu Met Thr Lys Lys Gln Val Phe Ile Phe Asp Ser Leu Val Lys Lys
                85                  90                  95

Cys Leu Phe Glu Val Leu Asn Thr Lys Asn Ile Phe Pro Gly Asp Val
            100                 105                 110

Asn Trp Phe Val Gln His Glu Trp Gly Lys Asp Gln Gly Trp His Cys
        115                 120                 125

His Val Leu Ile Gly Gly Lys Asp Phe Ser Gln Ala Gln Gly Lys Trp
    130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Asn Glu Trp Val Thr Leu Leu Thr Tyr Lys His Lys Gln
            180                 185                 190

Thr Lys Lys Asp Tyr Thr Lys Cys Val Leu Phe Gly Asn Met Ile Ala
        195                 200                 205

Tyr Tyr Phe Leu Thr Lys Lys Ile Ser Thr Ser Pro Pro Arg Asp
    210                 215                 220

Gly Gly Tyr Phe Leu Ser Ser Asp Ser Gly Trp Lys Thr Asn Phe Leu

```
            225                 230                 235                 240
Lys Glu Gly Glu Arg His Leu Val Ser Lys Leu Tyr Thr Asp Asp Met
                    245                 250                 255

Arg Pro Glu Thr Val Glu Thr Thr Val Thr Thr Ala Gln Glu Thr Lys
                    260                 265                 270

Arg Gly Arg Ile Gln Thr Lys Lys Glu Val Ser Ile Lys Thr Thr Leu
                    275                 280                 285

Lys Glu Leu Val His Lys Arg Val Thr Ser Pro Glu Asp Trp Met Met
                    290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                    325                 330                 335

Thr Lys Thr Ala Phe Asp Leu Ile Leu Glu Lys Ala Glu Thr Ser Lys
                    340                 345                 350

Leu Thr Asn Phe Ser Leu Pro Asp Thr Arg Thr Cys Arg Ile Phe Ala
                    355                 360                 365

Phe His Gly Trp Asn Tyr Val Lys Val Cys His Ala Ile Cys Cys Val
                    370                 375                 380

Leu Asn Arg Gln Gly Gly Lys Arg Asn Thr Val Leu Phe His Gly Pro
385                 390                 395                 400

Ala Ser Thr Gly Lys Ser Ile Ile Ala Gln Ala Ile Ala Gln Ala Val
                    405                 410                 415

Gly Asn Val Gly Cys Tyr Asn Ala Ala Asn Val Asn Phe Pro Phe Asn
                    420                 425                 430

Asp Cys Thr Asn Lys Asn Leu Ile Trp Val Glu Glu Ala Gly Asn Phe
                    435                 440                 445

Gly Gln Gln Val Asn Gln Phe Lys Ala Ile Cys Ser Gly Gln Thr Ile
                    450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Val Arg Ile Gly Cys
                    485                 490                 495

Glu Glu Arg Pro Glu His Thr Gln Pro Ile Arg Asp Arg Met Leu Asn
                    500                 505                 510

Ile His Leu Thr His Thr Leu Pro Gly Asp Phe Gly Leu Val Asp Lys
                    515                 520                 525

Asn Glu Trp Pro Met Ile Cys Ala Trp Leu Val Lys Asn Gly Tyr Gln
                    530                 535                 540

Ser Thr Met Ala Ser Tyr Cys Ala Lys Trp Gly Lys Val Pro Asp Trp
545                 550                 555                 560

Ser Glu Asn Trp Ala Glu Pro Lys Val Pro Thr Pro Ile Asn Leu Leu
                    565                 570                 575

Gly Ser Ala Arg Ser Pro Phe Thr Pro Lys Ser Thr Pro Leu Ser
                    580                 585                 590

Gln Asn Tyr Ala Leu Thr Pro Leu Ala Ser Asp Leu Glu Asp Leu Ala
                    595                 600                 605

Leu Glu Pro Trp Ser Thr Pro Asn Thr Pro Val Ala Gly Thr Ala Glu
                    610                 615                 620

Thr Gln Asn Thr Gly Glu Ala Gly Ser Lys Ala Cys Gln Asp Gly Gln
625                 630                 635                 640

Leu Ser Pro Thr Trp Ser Glu Ile Glu Glu Asp Leu Arg Ala Cys Phe
                    645                 650                 655
```

```
-continued

Gly Ala Glu Pro Leu Lys Lys Asp Phe Ser Glu Pro Leu Asn Leu Asp
            660                 665                 670
```